United States Patent
Zhou et al.

(10) Patent No.: US 9,217,700 B2
(45) Date of Patent: Dec. 22, 2015

(54) PIEZO ACTUATED FLUID DISPENSER FLUID CHARACTERIZATION

(71) Applicants: Xerox Corporation, Norwalk, CT (US); Palo Alto Research Center Incorporated, Palo Alto, CA (US)

(72) Inventors: Jing Zhou, Rochester, NY (US); Wei Hong, Amherst, MA (US); Steven E. Ready, Los Altos, CA (US)

(73) Assignees: XEROX CORPORATION, Norwalk, CT (US); PALO ALTO RESEARCH CENTER INCORPORATED, Palo Alto, CA (US)

( * ) Notice: Subject to any disclaimer, the term of this patent is extended or adjusted under 35 U.S.C. 154(b) by 399 days.

(21) Appl. No.: 13/762,271

(22) Filed: Feb. 7, 2013

(65) Prior Publication Data

US 2014/0216141 A1 Aug. 7, 2014

(51) Int. Cl.
| | |
|---|---|
| *G01N 11/00* | (2006.01) |
| *G01N 9/00* | (2006.01) |
| *G01N 29/036* | (2006.01) |
| *G01N 29/024* | (2006.01) |
| *G01N 29/46* | (2006.01) |
| *B41J 2/045* | (2006.01) |
| *G01N 11/16* | (2006.01) |
| *B41J 2/14* | (2006.01) |

(52) U.S. Cl.
CPC .............. *G01N 9/002* (2013.01); *B41J 2/04541* (2013.01); *B41J 2/04571* (2013.01); *B41J 2/04581* (2013.01); *G01N 11/16* (2013.01); *G01N 29/024* (2013.01); *G01N 29/036* (2013.01); *G01N 29/46* (2013.01); *B41J 2002/14354* (2013.01); *G01N 2011/0073* (2013.01); *G01N 2291/0228* (2013.01); *G01N 2291/02818* (2013.01)

(58) Field of Classification Search
CPC ....................... G01N 2011/0073; G01N 9/002
See application file for complete search history.

(56) References Cited

U.S. PATENT DOCUMENTS 6,247,354 B1 * 6/2001 Vig et al. ...................... 73/54.41
2011/0148967 A1 * 6/2011 Schippers ........................ 347/14

FOREIGN PATENT DOCUMENTS

| EP | 2 497 642 | | 9/2012 |
|---|---|---|---|
| JP | 2006035812 | | 2/2006 |
| JP | 2006035812 A | * | 2/2006 |
| WO | 2010/023135 | | 3/2010 |

OTHER PUBLICATIONS

European Search Report dated Jun. 12, 2014 from European Patent Application No. 14152422.3, pp. 1-6.
Antohe, Bogdan V. et al. The determination of the speed of sound in liquids using acoustic resonance in peizoelectric tubes. Measurement Science and Technology, Nov. 1, 1999, vol. 10, No. 11, pp. 1-5.

* cited by examiner

*Primary Examiner* — Paul West
(74) *Attorney, Agent, or Firm* — MH2 Technology Law Group LLP

(57) ABSTRACT

A technique, including a system and a method, for measuring a fluid property using a piezo-actuated fluid dispenser, is disclosed. The technique includes generating a pressure wave in a channel in the piezo-actuated fluid dispenser using a piezo element, detecting, using the piezo element, a residual pressure oscillation in the channel caused by the generating, obtaining a resonance frequency of the pressure oscillation, and determining, using the resonance frequency, the fluid property.

12 Claims, 6 Drawing Sheets

PIEZO ACTUATED FLUID DISPENSER FLUID CHARACTERIZATION

FIELD OF THE INVENTION

This invention relates generally to determining information about fluids used in piezo-actuated fluid dispensers, e.g., piezo inkjet printheads.

BACKGROUND OF THE INVENTION

Piezo-actuated fluid dispensers can be used for a variety of purposes, not limited to creating documents. To operate effectively, piezo-actuated fluid dispensers can be tuned according to certain properties of the fluids that they deploy.

SUMMARY

A technique, including a system and a method, for measuring a fluid property using a piezo-actuated fluid dispenser, is disclosed. The technique includes generating a pressure wave in a channel in the piezo-actuated fluid dispenser using a piezo element, detecting, using the piezo element, a residual pressure oscillation in the channel caused by the generating, obtaining a resonance frequency of the pressure oscillation, and determining, using the resonance frequency, the fluid property.

Various optional features of the above technique include the following. The fluid property can be viscosity or speed of sound. Where the property is speed of sound, the technique can include multiplying the resonance frequency by a constant dependent on properties of the channel. Where the property is speed of sound, the technique can include: generating a plurality of pressure waves in the channel in the piezo-actuated fluid dispenser using the piezo element, such that each of the plurality of pressure waves has a different dwell time, determining a period of oscillation at a power spectrum amplitude at the resonance frequency, and determining the speed of sound as a function of the period of oscillation. Where the property is viscosity, the technique can include: calculating a width of a resonance peak in a power spectrum of the residual pressure oscillation, and determining, based on the width, the viscosity. The width can be full width at half maximum, variance, or standard deviation. The technique can include adjusting at least one of fluid temperature and pressure waveform based on the fluid property. The technique can include obtaining calibration information based on a calibration fluid. Where the property is viscosity, the technique can include obtaining a fluid density parameter. Obtaining the fluid density parameter can include accessing a stored lookup table of fluid densities.

BRIEF DESCRIPTION OF THE DRAWINGS

Various features of the embodiments can be more fully appreciated, as the same become better understood with reference to the following detailed description of the embodiments when considered in connection with the accompanying figures, in which.

DESCRIPTION OF THE EMBODIMENTS

Reference will now be made in detail to the present embodiments (example embodiments) of the invention, which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

Piezo-actuated fluid dispenser technology can be used to print documents, but is by no means limited to such use. In general, piezo-actuated fluid dispenser technology can be used for additive manufacturing. For example, piezo-actuated fluid dispensers can apply many different fluid materials, not limited to ink, to a variety of substrates. Example fields of application include biology, medicine, printed electronics (e.g., organic printed electronics), photovoltaics, and 3D printing. Accordingly, throughout this disclosure, the term "ink" includes inks used in typical inkjet printing technologies, as well as any fluid that can be used in piezo-actuated fluid dispensers for any application.

Performance of piezo-actuated fluid dispensers depends in part on certain ink properties, such as speed of sound within the ink and ink viscosity. In particular, tuning parameters of piezo-actuated fluid dispensers (e.g., temperature, jetting waveform frequency, jetting waveform dwell time) depends on at least ink speed of sound and viscosity. Thus, measuring ink speed of sound and ink viscosity is helpful for improving and optimizing piezo-actuated fluid dispenser operation. However, it is neither time-efficient nor cost-effective to measure every ink using conventional analytic apparatuses, particularly in situations where many inks need to be evaluated. Although certain viscosities can be measured using a rheometer, the highest oscillation frequency of a typical rheometer is in the order of 100 Hz, far below typical piezo-actuated fluid dispenser jetting frequencies. Adding to the difficulties of measuring ink viscosities, viscosities of non-newtonian fluids, such as some inks, can change with shear rate. Further, measuring ink speed of sound presents its own challenges due to the lack of convenient ubiquitous analytical measurement apparatuses.

Various embodiments measure speed of sound in ink and ink viscosity using piezo-actuated fluid dispenser self-sensing circuitry. Embodiments can be used by, for example, ink formulators and end users, e.g., in biological applications of piezo-actuated fluid dispenser technologies.

Figure 1A:
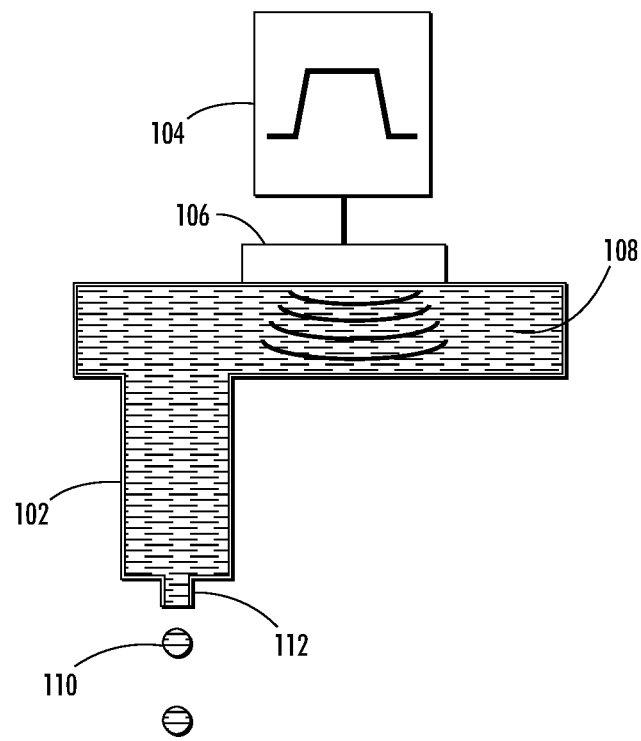
FIGS. 1A and 1B are schematic diagrams of single units of piezo-actuated fluid dispensers according to various embodiments.
Figure 1B:
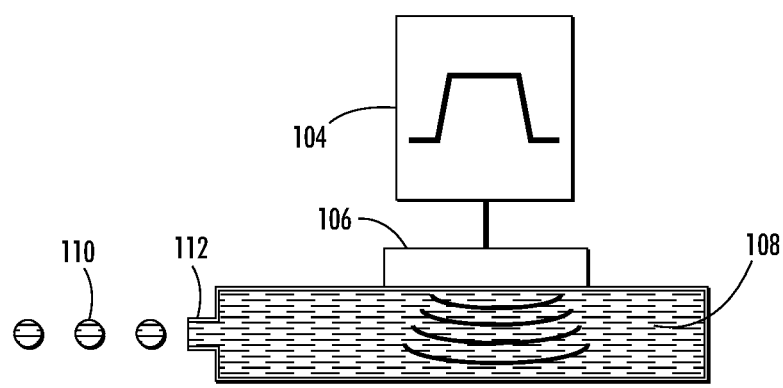

FIGS. 1A and 1B are schematic diagrams of single units of piezo-actuated fluid dispensers according to various embodiments. The dispenser includes channel 102, which contains the ink. Piezo element 106 acts as an actuator. Specifically, piezo element 106 deflects when a voltage is applied according to, for example, the following equation.

$$\begin{bmatrix} y \\ Q \end{bmatrix} = \begin{bmatrix} d & 1/k \\ C & d \end{bmatrix} \begin{bmatrix} V \\ F \end{bmatrix} \quad (1)$$

In Equation (1), y represents a displacement amount with force F caused by application of voltage V and charge Q to a piezo element having capacitance C, stiffness k, and a piezo charge constant of d. Application of voltage waveform 104 to piezo element 106 thus generates pressure wave 108 in ink channel 102. Pressure wave 108, in turn, may cause the piezo-actuated fluid dispenser to eject ink droplets 110 from nozzle 112.

Pressure wave 108 will, in general, keep oscillating in channel 102 after voltage waveform 104 is removed. This residual oscillation will eventually be damped out by fluid viscosity and channel structure (e.g., the walls of channel 102 not being perfectly elastic). Note that an amplitude of voltage waveform 104 may have an amplitude insufficient to cause ejection of ink droplets 110 from nozzle 112, yet still be sufficient to generate residual oscillations in channel 102.

Note that Equation (1) characterizes both displacement caused by applied voltage and generated voltage caused by mechanically induced displacement. That is, mechanically displacing a piezo element having capacitance C, stiffness k, and a piezo charge constant of d by a distance of y using force F will produce a charge Q at voltage V as described by Equation (1). Thus, as discussed below in reference to FIG. 2, piezo element 106 can be used to sense the residual oscillation in channel 102 after application of voltage waveform 104. The self-sensing signal is proportional to the total pressure on the surface of piezo element 106 caused by the residual oscillation.

Figure 2:
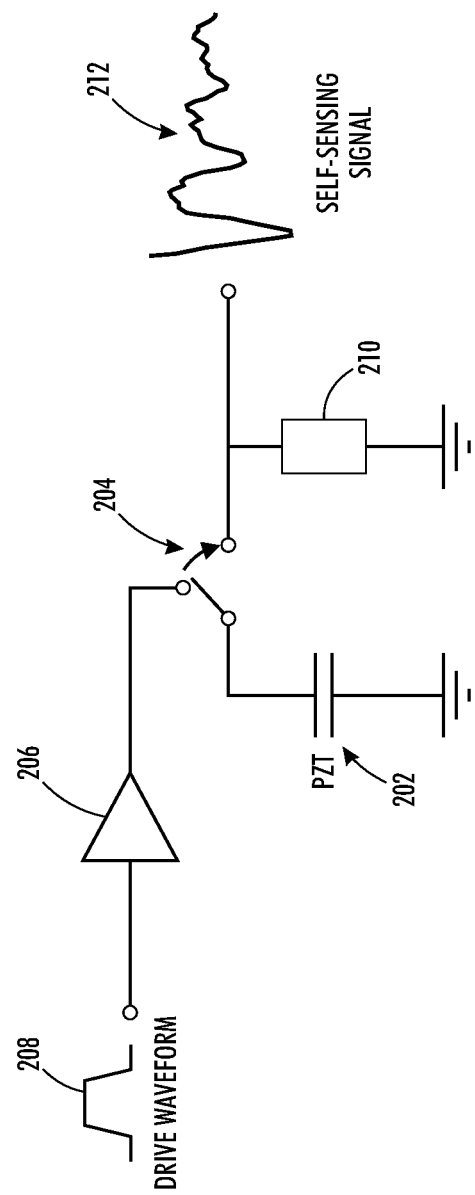
FIG. 2 is a schematic diagram of an example piezo-actuated fluid dispenser self-sensing circuit according to various embodiments.

FIG. 2 is a schematic diagram of an example piezo-actuated fluid dispenser self-sensing circuit according to various embodiments. Note that the self-sensing circuit depicted in FIG. 2 is exemplary only; many other self-sensing circuits can be used in the alternative. As such, the particular circuit of FIG. 2 is non-limiting. As depicted in FIG. 2, the self-sensing circuit includes piezo element 202, which can be disposed on a piezo-actuated fluid dispenser. Piezo element 102 is electrically coupled to switch 204, which can be, for example, an electronically controllable solid state device. Switch 204 can electrically couple piezo element 202 to amplifier 206, which can convey to piezo element 202 electrical drive waveform 208. After coupling drive waveform 208 to piezo element 202, switch 204 can operate to electrically disengage piezo element 202 from amplifier 206 and electrically couple piezo element 202 to resistor 210. Self-sensing signal 212 (e.g., voltage) is then present across resistor 210.

Switch 204 can have a switching speed on the order of tens of nanoseconds, for example. Residual oscillations can persist on the order of tens of microseconds. Thus, switch 204 can disengage piezo element 202 from drive waveform 208 and engage resistor 210 such that self-sensing signal 212 can capture essentially all of the residual waveforms appearing in an associated ink channel.

Figure 3:
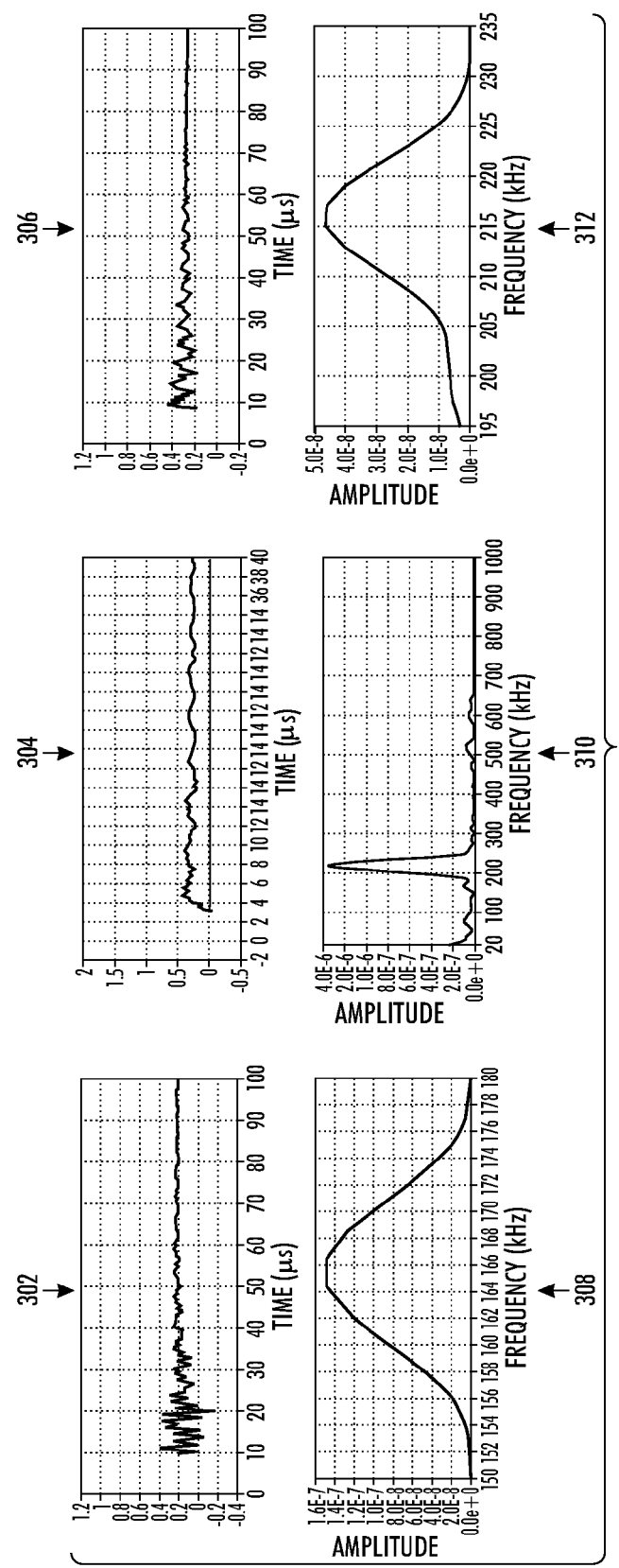
FIG. 3 is a collection of charts depicting piezo inkjet printhead self-monitoring circuit signal levels and power spectra for three different piezo inkjet printheads according to various embodiments.

FIG. 3 is a collection of charts depicting piezo inkjet printhead self-monitoring circuit signal levels and power spectra for three different piezo inkjet printheads according to various embodiments. The charts do not depict the initial pressure wave, which generally starts at t=0. Rather, the charts depict only the resulting residual oscillations. Thus, chart 302 depicts a self-sensing signal in a first example piezo inkjet printhead using a first example ink. The signal of chart 302 oscillates for approximately 40 micro-seconds. Chart 308 represents a power spectra corresponding to the self-sensing signal of chart 302. In particular, chart 308 depicts a resonant frequency of approximately 165 kHz. Chart 304 depicts a self-sensing signal in a second example piezo inkjet printhead using a second example ink. The signal of chart 304 oscillates for approximately 40 micro-seconds. Chart 310 represents a power spectra corresponding to the self-sensing signal of chart 304. In particular, chart 310 depicts a resonant frequency of approximately 220 kHz. Chart 306 depicts a self-sensing signal in a third example piezo inkjet printhead using a third example ink. The signal of chart 306 oscillates for approximately 40 micro-seconds. Chart 312 represents a power spectra corresponding to the self-sensing signal of chart 306. In particular, chart 312 depicts a resonant frequency of approximately 215 kHz.

The power spectra of charts 308, 310, and 312 can be obtained using known techniques, e.g., fast Fourier transforms, applied to the signals of charts 302, 304, and 306, respectively. Once power spectra are obtained, known techniques, e.g., peak detection, can be used to identify resonant frequencies. (One or more resonant frequencies can be detected; in such cases, some embodiments utilize a resonance frequency with a highest amplitude.) The techniques discussed in this paragraph can be implemented using, for example, hardware, software, or combinations thereof.

Certain embodiments obtain resonant frequencies of self-sensing signals of piezo-actuated fluid dispensers, as discussed above, and utilize the resonant frequencies to calculate speed of sound in the respective ink. A relationship between speed of sound and resonant frequency can be expressed according to, for example, Equation (2) below.

$$f = \alpha c \quad (2)$$

In Equation (2) above, f represents a resonant frequency (e.g., having a greatest amplitude) of a self-sensing signal of a piezo-actuated fluid dispenser containing an example ink, c represents a speed of sound in the example ink, and a represents a constant that depends only on the physical properties (e.g., physical configuration and temperature) of the channel of the piezo-actuated fluid dispenser. Once the parameter α is determined for a given piezo-actuated fluid dispenser and a given ink, the speed of sound for different inks can be calculated for different inks using Equation (2) and self-sensing signal data obtained from the piezo-actuated fluid dispenser.

Thus, some embodiments obtain and store the parameter a for later use in calculating a speed of sound. (Some embodiments obtain and store a plurality of values for α, each corresponding to a different temperature.) This can occur in a factory setting, in an end-user setting, or in a different setting. To calculate α (at a particular temperature and for a particular piezo-actuated fluid dispenser), a fluid with a known speed of sound can be used (referred to herein as a "calibration fluid"). Such calibration fluids include, for example, water, water and glycerol mixes, liquid wax, oil, etc. (For fresh water, a speed of sound at 25° C. is approximately 1497 m/s and at 15° C. is approximately 1466 m/s.) To determine α, an embodiment determines an operating temperature, retrieves a speed of sound for the calibration liquid at the operating temperature, uses the piezo-actuated fluid dispenser self-sensing signal to determine a value for its resonance frequency, and solves Equation (2) for α. Some embodiments store values for α in association with temperatures in persistent memory included in, or attached to, piezo-actuated fluid dispenser.

Some embodiments can determine a speed of sound for an ink in use with a piezo-actuated fluid dispenser as follows. The embodiments obtain a self-sensing signal, calculate its power spectrum or fast Fourier transform, and use it to determine a resonance frequency. The embodiments then retrieve (e.g., from an electronic persistent memory) a value for α appropriate for the current operational temperature, then use Equation (2) to solve for the speed of sound c.

The above technique is but one way to calculate an ink speed of sound. Another technique for calculating ink speed of sound is discussed in detail below in reference to FIG. 4.

Figure 4:
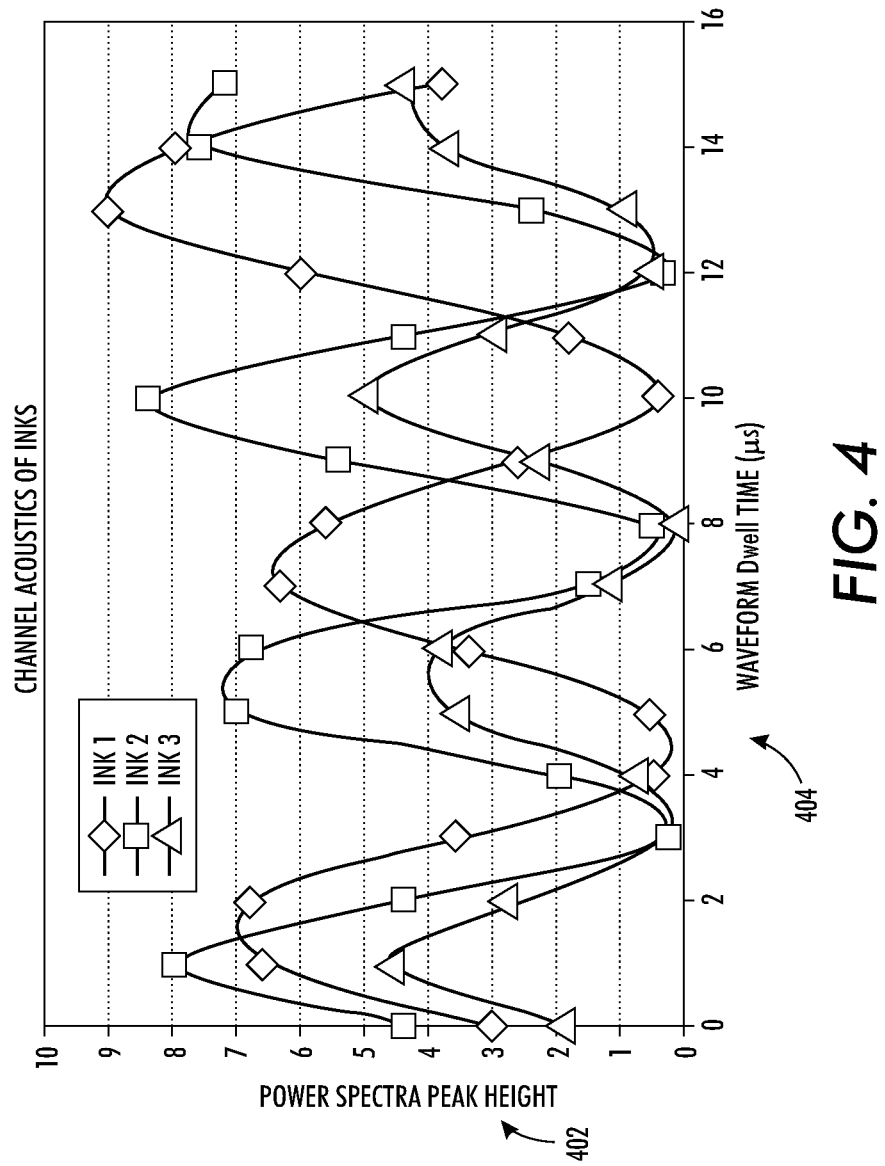
FIG. 4 is a chart of resonance frequency amplitude oscillations for various example inks according to various embodiments.

FIG. 4 is a chart 404 of resonance frequency amplitude oscillations for various example inks according to various embodiments. Such resonance frequency amplitude oscillations can be used to determine speed of sound as discussed presently. Channel acoustics in a piezo-actuated fluid dispenser change with drive waveforms. More specifically, trapezoidal waveforms of different lengths (dwell times) cause power spectrum amplitudes at the channel resonance frequency to oscillate as a function of dwell time. This, chart 404 depicts power spectra resonance frequency amplitudes for three example inks as a function of drive waveform dwell time. For example, for Ink 1, a trapezoidal drive waveform with zero dwell time corresponds to a power spectrum resonance frequency height of three, whereas a trapezoidal drive waveform with a dwell time of two micro-seconds corresponds to a power spectrum resonance frequency height of about 6.8. Notably, the period of oscillation of power spectra resonance frequencies according to dwell time duration is inversely proportional to the speed of sound in the ink in use.

Thus, some embodiments determine ink speed of sound using resonance frequency information as follows. First, such embodiments use a calibration fluid to determine the proportionality constant for particular temperatures. Such embodiments can store values for such constants in persistent memory included in or coupled to the piezo-actuated fluid dispensers. To determine a speed of sound for a new ink, the embodiments issue a number of trapezoidal drive waveforms with different dwell times and record the corresponding power spectrum resonance frequency peak heights. (The number of such drive waveforms is any number sufficient to discern a period of resonant frequency peak heights.) The embodiments then determine a period of oscillation for the resonant frequency peak heights, retrieve a proportionality constant for the associated temperature from memory, and use these parameters in a linear equation determined by the appropriate proportionality constant to calculate the speed of sound for the new ink at the operational temperature.

Other techniques for calculating ink speed of sound based on the resonant frequency of a piezo-actuated fluid dispenser channel using a piezo self-sensing signal are possible, not limited to the techniques discussed above in reference to FIGS. 3 and 4.

A technique for determining ink viscosity using a resonance frequency detected by a self-sensing signal of a piezo-actuated fluid dispenser is discussed below in reference to FIG. 5.

Figure 5:
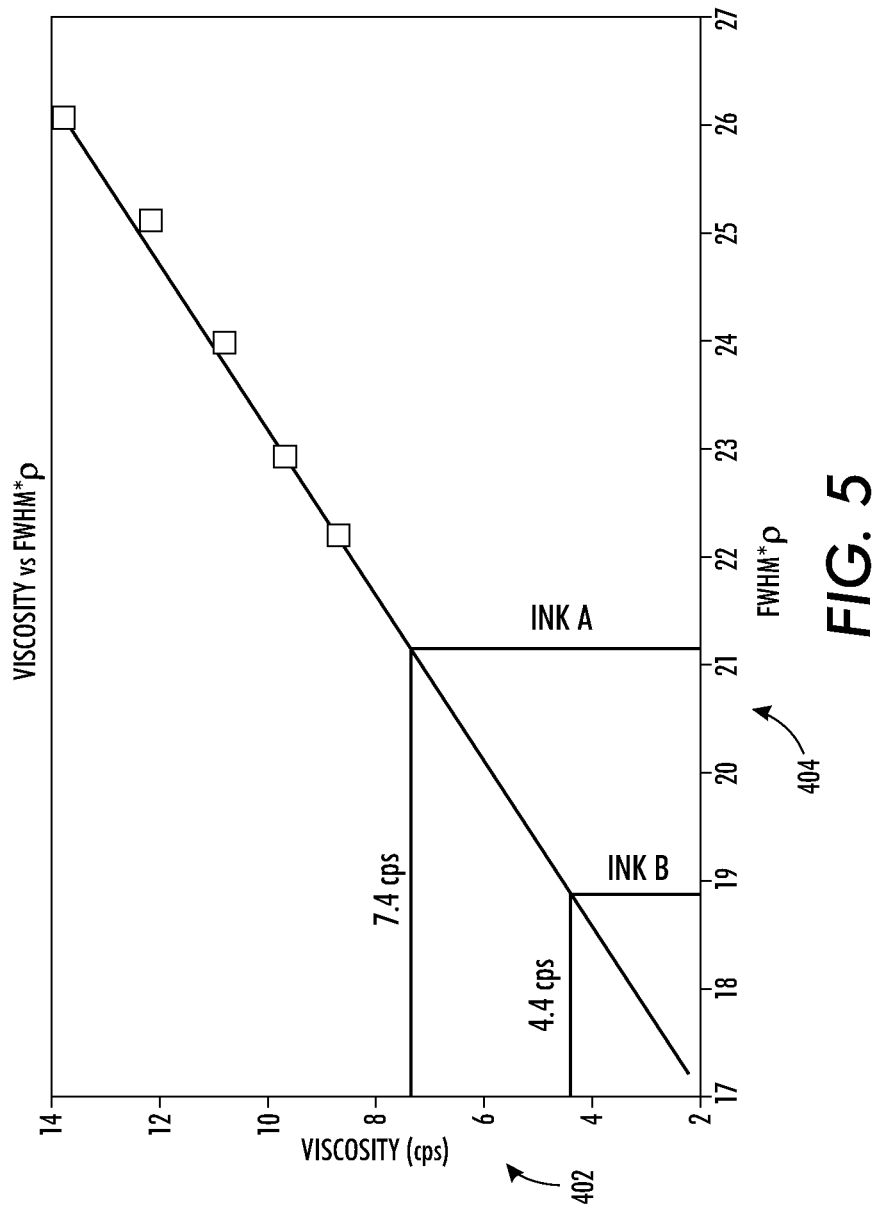
FIG. 5 is a chart depicting an example master curve for a viscosity calculation according to various embodiments.

FIG. 5 is a chart depicting an example master curve for a viscosity calculation according to various embodiments. In general, a self-sensing signal is a collection of under-damped oscillations. There are two primary sources of damping in a piezo-actuated fluid dispenser, namely, damping due to fluid viscosity and damping due to structural inelasticity. Damping coefficients can be estimated from, e.g., full-width at half-maximum ("FWHM") of resonance peaks. An example expression of this relationship appears below as Equation (3).

$$FWHM \propto \frac{\beta_s + \beta_v}{\rho} \quad (3)$$

In Equation (3), FWHM represents the width of a self-sensing signal power spectrum at resonant frequency at half of its maximum magnitude, "ρ" represents ink density, the symbol "∝" represents proportionality, $\beta_s$ represents damping due to structural inelasticity, and $\beta_v$ represents damping due to fluid viscosity. For a given piezo-actuated fluid dispenser, $\beta_s$ is constant. Accordingly, with Equation (3) it is possible to construct a known relationship curve between ink viscosity and the product FWHM×ρ with a known set of fluids. That is, given multiple triples (v, FWHM, ρ) for multiple fluids or fluid temperatures, where the symbol "v" represents viscosity, it is possible to construct a map from FWHM×ρ to fluid viscosity that applies to an arbitrary fluid. These triples can be obtained using a calibration fluid or a wax ink with known properties at multiple temperatures. The Table below represents a portion of such data.

TABLE

|      | WI @ 100° C. | WI @ 105° C. | WI @ 110° C. | WI @ 115° C. | WI @ 120° C. |
|------|------|------|------|------|------|
| FWHM | 13.74 | 12.15 | 10.78 | 9.650 | 8.680 |
| ρ    | 0.82210 | 0.81905 | 0.81600 | 0.81295 | 0.80990 |

The above table includes values for FWHM and ρ for example wax ink ("WI") at various temperatures. Properties for this wax ink are known, such that the corresponding viscosities for these conditions are also known. From these parameters, the curve of FIG. 5 can be extrapolated using known techniques, e.g., least squares.

The curve of FIG. 5 can then be used to obtain viscosity values for new inks based on FWHM as measured using a self-sensing signal and based on known densities. Thus, some embodiments store density values of various inks at various temperatures, e.g., in persistent memory included in or coupled to the associated piezo-actuated fluid dispenser. A user can supply the identify of a given ink to, e.g., a user interface, and the system can retrieve the associated value for ρ. At that point, the system can match the product FWHM×ρ to the corresponding viscosity based on the curve of FIG. 5 (or an analogous curve based on additional or alternative measurements).

Figure 6:
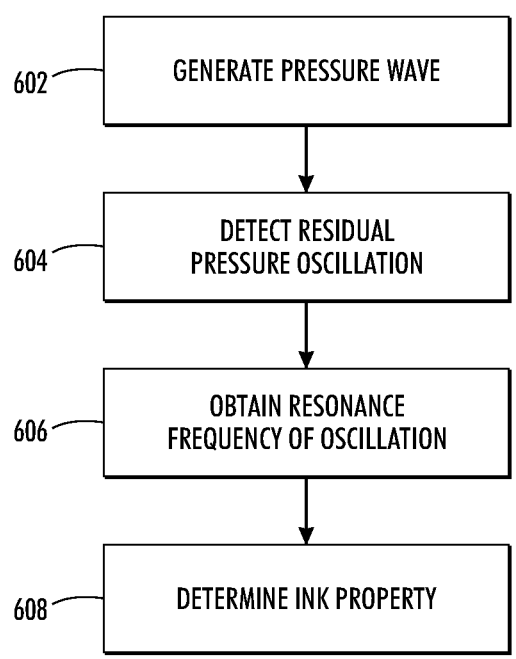
FIG. 6 is a flowchart depicting an example process according to various embodiments.

FIG. 6 is a flowchart depicting an example process for determining ink properties using a resonance frequency detected using a self-sensing signal according to various embodiments. The process or FIG. 6 can be implemented using, for example, a piezo-actuated fluid dispenser as depicted in FIGS. 1 and 2, as well as software, hardware, or a combination thereof.

At block 602, the system applies a drive waveform to the piezo element of a piezo-actuated fluid dispenser (e.g., piezo element 202 of FIG. 2) and generates a pressure wave inside the channel. The drive waveform can have known parameters such as amplitude and dwell time. At block 604, the system detects residual pressure oscillations, e.g., by switching switch 204 of FIG. 2, to provide a self-sensing signal. At block 606, the system obtains a resonance frequency of the residual pressure oscillations using, e.g., a fast Fourier transform.

At block 608, the system determines an ink property using the resonance frequency as an input to one of the techniques discussed herein in reference to FIGS. 3-5 to determine speed of sound and/or viscosity.

Once values for speed or sound and/or ink viscosity are determined, the system can tune parameters of the piezo-actuated fluid dispenser (e.g., temperature, jetting waveform frequency, jetting waveform dwell time) according to known techniques.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." The term "at least one of" is used to mean one or more of the listed items can be selected.

Certain embodiments can be performed as a computer program or set of programs. The computer programs can exist in a variety of forms both active and inactive. For example, the computer programs can exist as software program(s) comprised of program instructions in source code, object code, executable code or other formats; firmware program(s), or hardware description language (HDL) files. Any of the above can be embodied on a transitory or non-transitory computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A method of measuring a fluid viscosity using a piezo-actuated fluid dispenser, the method comprising:
   generating a pressure wave in a channel in the piezo-actuated fluid dispenser using a piezo element;
   detecting, using the piezo element, a residual pressure oscillation in the channel caused by the generating;
   obtaining a resonance frequency of the residual pressure oscillation;
   calculating a width of a resonance peak at the resonance frequency in a power spectrum of the residual pressure oscillation; and
   determining, based on the width, the fluid viscosity.

2. The method of claim 1, wherein the width is one of full width at half maximum, variance, and standard deviation.

3. The method of claim 1, further comprising adjusting at least one of fluid temperature and pressure waveform based on the fluid viscosity.

4. The method of claim 1, further comprising obtaining calibration information based on a calibration fluid.

5. The method of claim 1, further comprising obtaining a fluid density parameter.

6. The method of claim 5, wherein the obtaining a fluid density parameter comprises accessing a stored lookup table of fluid densities.

7. A system for measuring a fluid viscosity comprising:
   a piezo-actuated fluid dispenser comprising a channel, the piezo-actuated fluid dispenser configured to dispense fluid, the channel configured to contain fluid;
   a piezo element configured to generate a pressure wave in the channel, the piezo element further configured to provide a signal to a processor indicating a residual pressure oscillation in the channel;
   a processor configured to obtain a resonance frequency of the pressure oscillation;
   a processer configured to calculate a width of a resonance peak at the resonance frequency in a power spectrum of the residual pressure oscillation; and
   a processor configured to determine, based on the width, the fluid viscosity.

8. The system of claim 7, wherein the width is one of full width at half maximum, variance, and standard deviation.

9. The system of claim 7, further comprising a processor configured to adjust at least one of fluid temperature and pressure waveform based on the fluid viscosity.

10. The system of claim 7, further comprising a processor configured to obtain calibration information based on a calibration fluid.

11. The system of claim 7, further comprising a processor configured to obtain an fluid density parameter.

12. The system of claim 11, further comprising a persistent memory storing a lookup table of fluid densities.

* * * * *